(12) United States Patent
Jang

(10) Patent No.: US 10,034,962 B2
(45) Date of Patent: Jul. 31, 2018

(54) IMPLANT FOR BONE-GRAFT AND A METHOD FOR BONE-GRAFTING USING THE SAME

(71) Applicant: Jae Woo Jang, Daegu (KR)

(72) Inventor: Jae Woo Jang, Daegu (KR)

( * ) Notice: Subject to any disclaimer, the term of this patent is extended or adjusted under 35 U.S.C. 154(b) by 0 days.

(21) Appl. No.: 15/633,769

(22) Filed: Jun. 27, 2017

(65) Prior Publication Data

US 2017/0290952 A1    Oct. 12, 2017

Related U.S. Application Data

(63) Continuation of application No. 14/405,785, filed as application No. PCT/KR2014/004896 on Jun. 2, 2014, now abandoned.

(51) Int. Cl.
| | |
|---|---|
| *A61F 2/02* | (2006.01) |
| *A61L 27/34* | (2006.01) |
| *A61L 27/36* | (2006.01) |
| *A61C 8/00* | (2006.01) |
| *A61C 8/02* | (2006.01) |
| *A61F 2/28* | (2006.01) |

(52) U.S. Cl.
CPC ............ *A61L 27/34* (2013.01); *A61C 8/0006* (2013.01); *A61C 8/0092* (2013.01); *A61F 2/2803* (2013.01); *A61L 27/3608* (2013.01); *A61L 27/3691* (2013.01); *A61F 2002/2839* (2013.01); *A61F 2310/00359* (2013.01); *A61L 2430/02* (2013.01); *A61L 2430/12* (2013.01)

(58) Field of Classification Search
CPC ........... A61F 2/2803; A61F 2002/2839; A61B 17/0057; A61B 17/1688; A61C 8/0092
See application file for complete search history.

(56) References Cited

U.S. PATENT DOCUMENTS

| | | |
|---|---|---|
| 4,430,760 A | 2/1984 | Smestad |
| 2008/0147197 A1 | 6/2008 | McKay |

FOREIGN PATENT DOCUMENTS

KR    10-2010-0074860 A    7/2010

*Primary Examiner* — Brian Dukert
(74) *Attorney, Agent, or Firm* — Revolution IP, PLLC

(57) ABSTRACT

An implant for bone-graft insertedly placed in a procedure pore, the implant includes a bone organism having a lump shape, and a protective film coated to cover an overall outer surface of the bone organism as to form an absorbent membrane. After the implant is insertedly placed in the procedure pore, the absorbent member is absorbed into a body and dissolved as time passes. The implant for the bone-graft may be applied to diverse procedures performed for hone-graft not only in a dental surgery but also in orthopedics or a plastic surgery.

5 Claims, 6 Drawing Sheets

Fig. 4
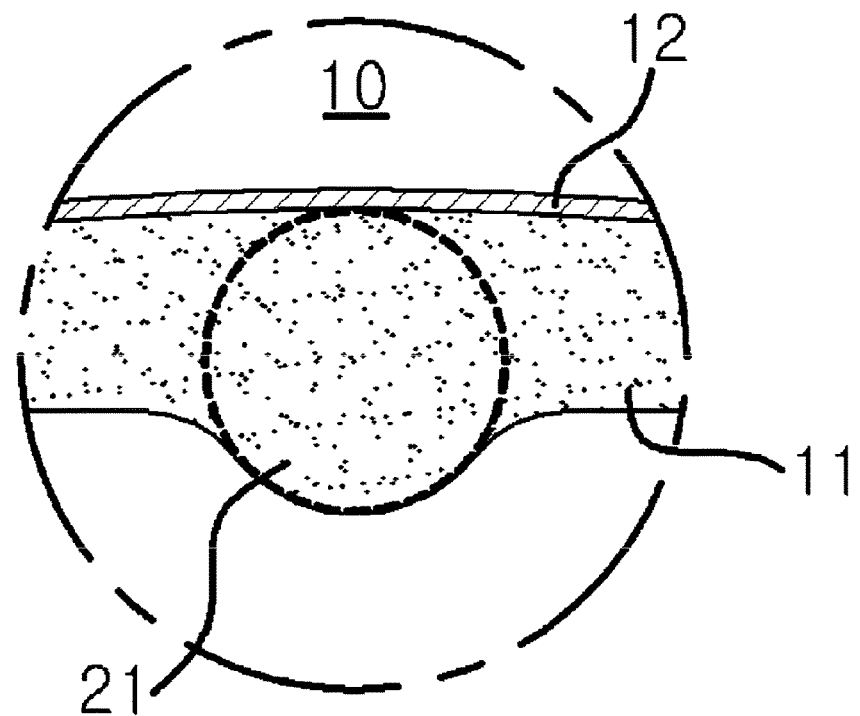
[Fig. 5]
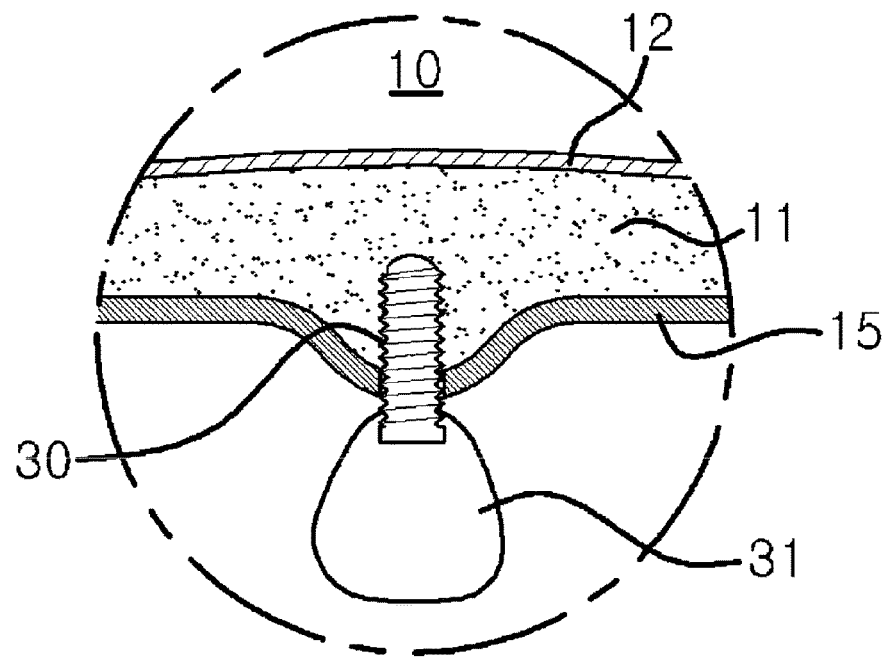

IMPLANT FOR BONE-GRAFT AND A METHOD FOR BONE-GRAFTING USING THE SAME

CROSS REFERENCE TO PRIOR APPLICATIONS

This application is a Continuation of U.S. patent application Ser. No. 14/405,785 filed on Dec. 5, 2014, which is a National Stage Application of PCT International Patent Application No. PCT/KR2014/004896 filed on Jun. 2, 2014, under 35 U.S.C. § 371, which is hereby incorporated by reference in its entirety.

BACKGROUND

Embodiments of the disclosure relate to an implant for bone-graft, more particularly, to an implant for bone-graft and a method for bone-grafting, using the same, which is performed in Sinus Lift performed for a patient's condition prior to an implant procedure.

Bone-grafting is used for broad purposes including bony defect preservation, osteogenic stimulus or synarthrosis, arthroereisis or anti-dislocation. Fresh autogenous bone graft is the best and homo-bone-graft or hetero-bone-graft is performed instead of the autogenous bone-graft. A long bone is the most frequently used bone used in bone-grafting. Not only the long bone, a tibia, a fibula or a rib is used in the bone-grafting. Most of the grafted bone is absorbed into an existing bone tissue. At the same time, the grafted bone is gradually replaced as a bone tissue newly generated by cell division.

The bone-grafting may be used in diverse medical fields and the present disclosure may be applied to a corresponding medical field. Hereinafter, an artificial medical implant procedure is selected among the diverse medical fields as a typical example. Bone-grafting is performed in an artificial medical implant procedure frequently, not every time.

In a broadly performed artificial medical implant procedure, an artificial titanium dental root capable of replacing a lost dental root is placed and conglutinated in an alveolar bone to be overlaid with an artificial tooth, such that a function of the teeth can be recovered. Such a conventional artificial medical implant procedure can be performed simply, with damaging no neighboring teeth. Also, a usage period of the procedure is semi-permanent and the procedure is then broadly used.

In case a dental root is healthy, the artificial medical implant procedure can be applied easily. Otherwise, it is not easy to apply the artificial medical implant procedure and a preparation process has to be performed before performing the artificial medical implant procedure. Especially, a maxillary sinus is a portion difficult to perform the procedure. The maxillary sinus is provided in each side of a cheekbone is filled with air, to reduce a weight of a head. The maxillary sinus is connected with a nasal cavity to ventilate air. If an infection is generated in the maxillary sinus, a sinus infection and the like can occur. When the maxillary sinus is located down, in other words, toward teeth, it is called "maxillary sinus pneumatization". In case a nasal pressure (nose wind), the maxillary sinus pneumatization can occur frequently. In addition, the maxillary sinus pneumatization can occur more frequently, if a tooth is lost. Accordingly, the amount of the dental root where an implant, in other words, an artificial root will be placed could be reduced. In this instance, a prior surgery for increasing the amount of the dental root is performed frequently.

When an artificial medical implant is placed because of maxillary sinus pneumatization and periodontitis, different procedures are used based on a patient's condition. In case the patient's bone is quite small, for instance, 2~3 mm of the patient's bone remains, a window surgery is performed. In case 4 mm or more of the patient's bone remains, sinus lift which is crestal approach is performed.

The sinus lift is a method of crestal approach and the window surgery is a method of lateral approach. In the sinus lift as the crestal approach, an artificial bone can be provided or not. When an artificial bone is provided, it can be called "BAOSFE (Bone Added Osteotome Sinus Floor)". When no artificial bone is provided, it is called "OSFE (Osteotome Sinus Floor Elevation)".

If a maxillary sinus layer membrane is penetrated in case the artificial bone is provided, artificial bone powder comes into the maxillary sinus through the maxillary sinus membrane to block an ostium connected with the nose to cause an infection. It is typical to provide no artificial bone in the crestal approach. Also, the crestal approach is not directly seen by an operator, which is a blind technique. It is difficult to identify whether the maxillary sinus membrane is torn during the sinus lift, such that it can be difficult to insert an artificial bone.

In contrast, in the lateral approach, a gum is cut away and a gum flap is completely open. The surgery is performed in such a state and the operator can directly see the maxillary sinus and identify whether the maxillary sinus pneumatization is torn. However, the window surgery is highly risky and the patient could be worried. Accordingly, the crestal approach is selected and performed.

Korean Patent No. 10-2008-0133404 discloses a liquid injection apparatus for lift membrane lift which can lift a sinus membrane by injecting liquid to lift a maxillary sinus membrane to prevent damage of the sinus lift and to secure the height of a useable bone root for placing an implant.

However, the apparatus is only means for preventing tearing of the sinus membrane and it has no relation with overcoming fatal problems which occurs after tearing the sinus membrane.

SUMMARY

To solve the problems, exemplary embodiments of the disclosure provide an implant for bone-graft which may allow bone-graft performed easily and rapidly, in case bone-graft is performed in a medical field, and a method for bone-grafting, using the implant.

More specifically, exemplary embodiments of the present disclosure provide an implant for bone-graft which prevents artificial bone powder from coming into a sinus even when a sinus membrane is raptured, in case of performing bone-grafting when an amount of an alveolar bone where an artificial dental root will be placed is small, and a method for bone-grafting, using the implant. Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the disclosure and claims hereof as well as the appended drawings.

To achieve these objects and other advantages and in accordance with the purpose of the embodiments, as embodied and broadly described herein, an implant for bone-graft insertedly placed in a procedure pore includes a bone organism having a lump shape; and a protective film coated to cover an overall outer surface of the bone organism as to form an absorbent membrane. After the implant is insertedly placed in the procedure pore, the absorbent member is absorbed into a body and dissolved as time passes.

The bone organism may be one of an allograft bone, a heterograft bone, an autograft bone and a synthetic bone. The allograft bone is a cortical bone taken from a tissue donor, the cortical bone being frozen and dried without deliming.

In another aspect of the present disclosure, the procedure pore may be provided in an alveolar bone by drilling in sinus lift prior to the implant procedure.

In a further aspect of the present disclosure, the absorbent membrane may be a collagen extracted from a hetero-biological material.

In a still further aspect of the present disclosure, a method for bone-grafting, using an implant for bone-graft insertedly placed in a procedure pore, the implant includes a bone organism having a lump shape; and a protective film coated to cover an overall outer surface of the bone organism as to form an absorbent membrane. After the implant is insertedly placed in the procedure pore, the absorbent member is absorbed into a body and dissolved as time passes, the method includes: forming a procedure pore in an alveolar bone; lifting a sinus membrane by a pressure applied to the sinus membrane by sequentially inserting the implant in the procedure pore.

In a still further aspect of the present disclosure, a method for bone-grafting, using an implant for bone-graft insertedly placed in a procedure pore, the implant includes a bone organism having a lump shape; and a protective film coated to cover an overall outer surface of the bone organism as to form an absorbent membrane. After the implant is insertedly placed in the procedure pore, the absorbent member is absorbed into a body and dissolved as time passes, the method includes: forming a procedure pore in an alveolar bone; sequentially filling the plurality of the implants into the procedure pore; and filling a powder type bone organism for bone-graft in a gap between the implants for the bone-graft.

The embodiments have following advantageous effects. When performing the bone-grafting in a medical field, implants configured of unit organisms may be used and it is easy and rapid to perform the implanting. Bone powder separated from the bone tissue is prevented from coming into an unexpected area. Accordingly, stability of the procedure may be enhanced.

For instance, even if the sinus membrane is raptured or damaged during the sinus lift in the bone-grafting performed prior to the implanting, the bone tissue filled in the procedure pore may not come into the sinus. The protective film formed of the absorbent membrane is holding the bone tissue. While the protective film is holding the bone tissue, the sinus membrane is restored.

Furthermore, only when the implant is just inserted in the procedure pore, the window surgery can be performed. Accordingly, the operation time can be reduced and the patient's inconvenience can be removed advantageously. Various methods may be applied. Using the implant according to the embodiments of the present disclosure, the sinus membrane may be lifted and the bone-graft may be performed easily in a procedure pore. The objectives and other advantages of the invention may be realized and attained by the structure particularly pointed out in the written description and claims hereof as well as the appended drawings.

BRIEF DESCRIPTION OF THE DRAWINGS

FIGS. 3, 4 and 5 are diagrams illustrating a process of performing an implant procedure in case the implant for bone-graft according to exemplary embodiments of the present disclosure is applied;

FIG. 7 is a front sectional diagram and FIG. 8 is a lateral sectional diagram.

DETAILED DESCRIPTION

Figure 1:
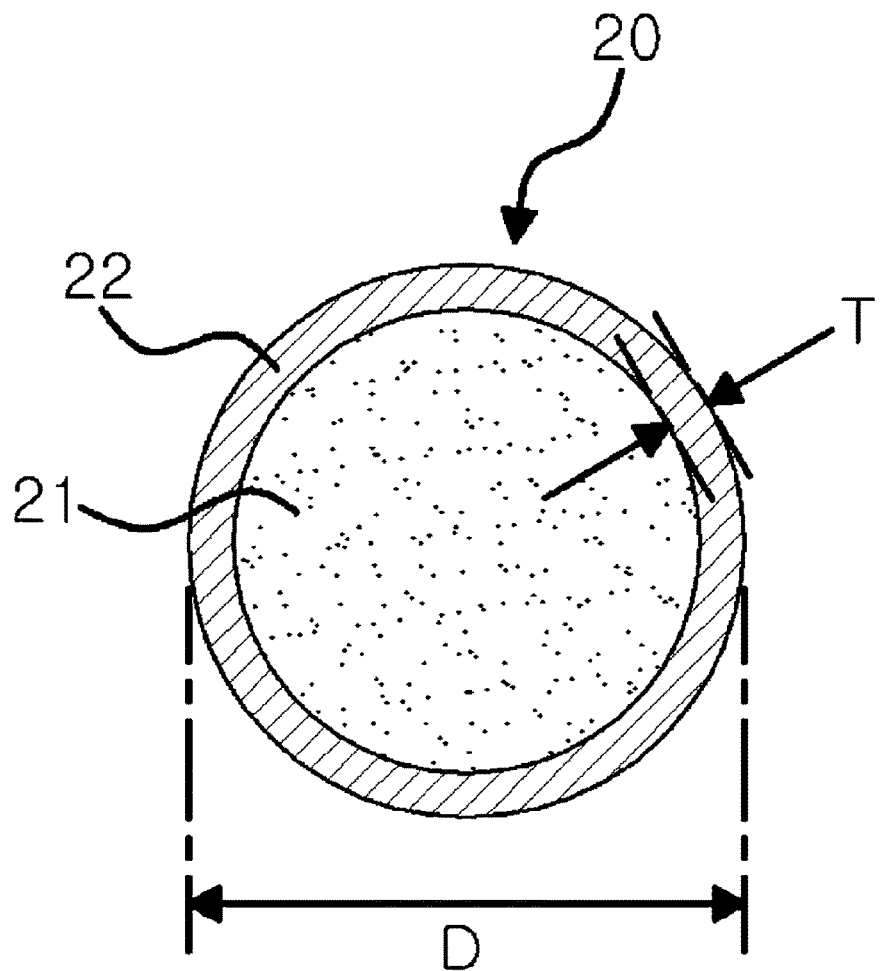
FIG. 1 is a sectional diagram of an implant for bone-graft according to exemplary embodiments of the present disclosure.
Figure 2:
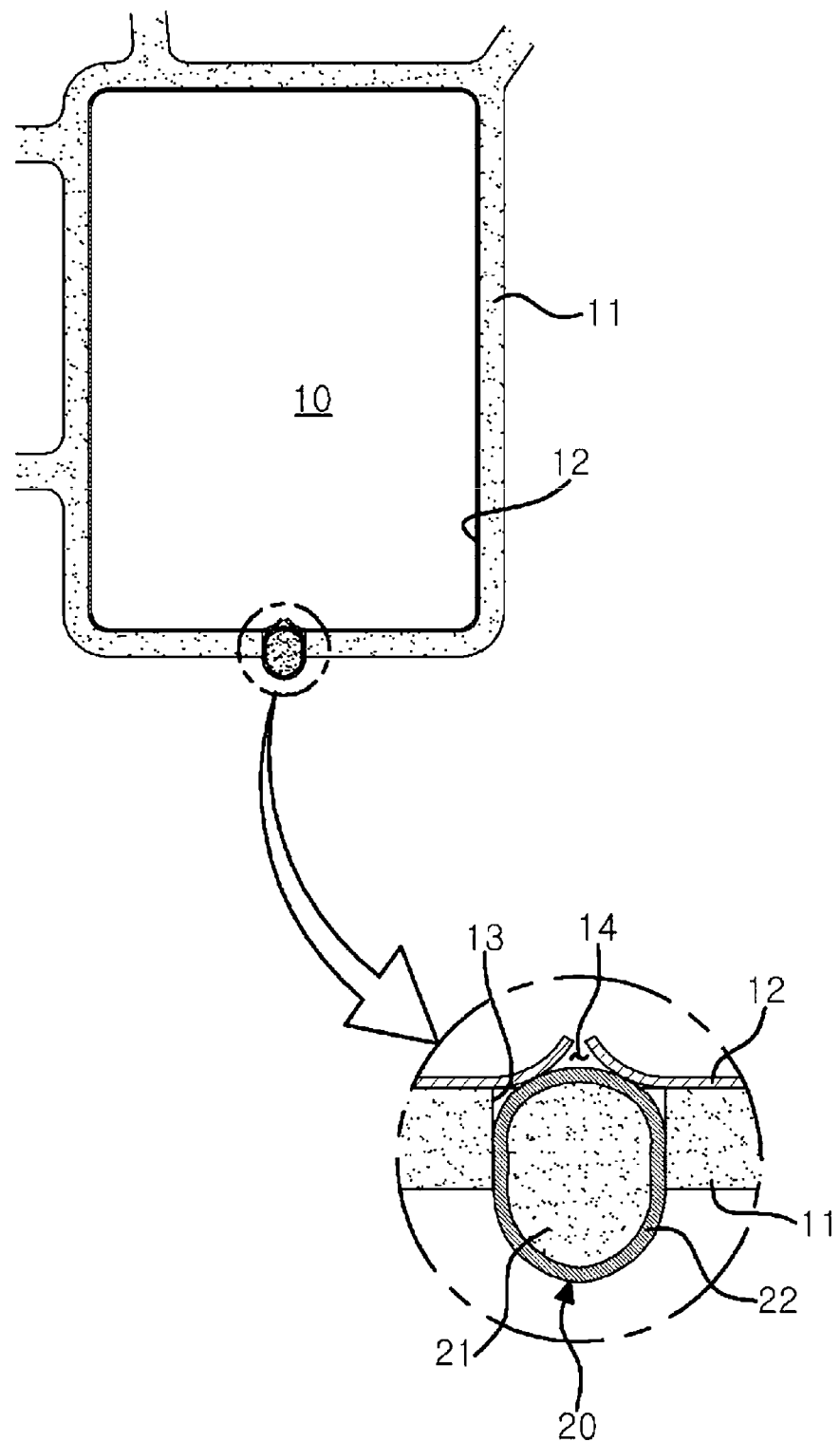
FIG. 2 is a schematic diagram of a human body to describe a state where the implant for the bone-graft according to exemplary embodiments of the present disclosure is insertedly placed.

Hereinafter, exemplary embodiments of the disclosure will be described in detail, referring to the accompanying drawings. Referring to FIGS. 1 and 2, an implant for bone-graft according to exemplary embodiments of the present disclosure.

The implant 20 according to the embodiments of the disclosure may be used to compensate a lost bone tissue or to change bone morphogenesis in various medical fields such as orthopedics, plastic surgery, dental surgery. Hereinafter, bone-grafting which is performed in an artificial medical implant in the dental surgery is embodied to describe the present disclosure, for convenient explanation. Scopes of the claims of the present disclosure are not limited by differences in purposes of a surgery or medical fields.

The implant 20 according to the embodiments of the present disclosure may be used in sinus lift performed prior to an artificial medical implant procedure. A method for using the implant 20, in other words, a procedure method using the implant 20 will be described later. Hereinafter, a structure of the implant 20 will be described.

The implant 20 having a cell body is insertedly placed in a procedure hole 13 provided in an alveolar bone 11 generated by drilling, an accident or natural occurrence. The implant 20 includes a bone organism 21 and a protective film 22. The bone organism 21 may be an allograft bone capable of enhancing osteoconduction. The allograft bone is a cortical bone gained from a tissue donor that the cortical bone is frozen and dried, without deliming. However, the bone organism 21 may be the patient's one separated from the other area for implanting. Or, the bone organism 21 may be a hetero-graft bone made of a bovine bone, a porcine bone and a horse bone or a synthetic bone made of hydroxyapatite and tricalcium phosphate. It is not necessary for the bone organism 21 to be circular-shaped and the bone organism 21 may be naturally-curved.

The bone organism 21 is a lump of powder. In this instance, the capacity of the bone organism 21 may be 0.05, 0.1, 0.2, 0.3, 0.5 or 1 cc. the size of a particle may be 200~850 μm. The bone organism 21 may be a chip type. In this instance, the capacity of the bone organism 21 may be 0.25, ~0.5 or 1.0 cc and a diameter of a powder particle may be 850~1,500 μm. Also, the bone organism 21 may be a gel type.

The protective film 22 may be an absorbent membrane and it is fixedly glued together with an outer surface of the bone organism 21, while covering the overall outer surface like fruit flesh or dumpling skin. The protective film 22 is coated on the bone organism 21 in a method of immersion coating. The protective film 22 may be a porous material for penetrating a bone cell there through. Bone cells are dispersed into the protective film 22 through cell division. During this process, the protective film 22 is absorbed in a human body to be dissolved and the bone cells are filled in the area where the protective film 22 is dissolved.

A material equally used in the same technical field is provided as the protective film 22. In 4 months after placing it in a human body part, the protective film 22 may be absorbed into the body and dissolved. As long as performing a similar function, the protective film 22 may be selected according to a user's need and it may be a material which will be developed in the future.

The thickness (T) of the protective film 22 may be determined enough to hold the bone organism 21 until a damaged sinus membrane (12, sinus membrane which will be described later) is healed and restored. It is meaningless to determine the thickness uniformly. Accordingly, the thickness of the protective film 22 may be 0.5~1.5 mm.

In one embodiment of the present disclosure, various sizes of the bone organism 21 and the implant 20 may be provided. For instance, a diameter (D) of the implant 20 may be 3, 5 or 7 mm.

Hereinafter, the absorbent membrane (hereinafter, just "the membrane") introduced as a material of the protective film 22 above will be described. The membrane is well known medical material as collagen extracted from a hetero-biological material (e.g., a bovine pericardium). The membrane is used after bone-graft and it may block inlet of an epithelial tissue and allow only a bone cell to grow. That is why the membrane has a micro-pore for penetrating not the epithelial tissue but the bone cell there through. The membrane is a well-known material which is absorbent into an enzyme and it takes 15~16 weeks for the membrane to be absorbed completely. During those weeks, the membrane is employed as a barrier for blocking the inlet of the epithelial tissue into the bone-graft area.

A surface of the membrane has a loose collagen structure in a 10 um-pore-net shape. The surface of the membrane has a structure which is in favor of ingrowth & vitalization of a connective tissue (e.g., FDA approval 510(K) Number K970851). The membrane is soaked in distilled water sufficiently before used.

Referring to FIGS. 2 through 5, a procedure method using the implant 20 according to embodiments of the disclosure will be described. FIGS. 2 through 5 show a procedure method using the implant 20 according to embodiments of the present disclosure will be described. FIGS. 2 through 5 show sinus lift which is crestal approach. The sinus lift is performed in case at least 5% of the alveolar bone remains. As an operator cannot see the sinus membrane 12 directly, the sinus lift is performed as blind technique.

Processes of the procedure using the implant 20 will be described as follows. FIG. 2 is a schematic diagram of a structure of a sinus 10 where bone-graft is performed. The sinus 10 has a hollow shape and the sinus membrane 12 is fixedly glued together with a surface of a bone organism forming the sinus 10.

After crestal cut, using a mess after anesthesia, a flap is separated. In case a remaining alveolar bone is 5 mm, drilling is performed as deep as 5 mm to form a procedure pore 13 and the plant 20 is inserted in the procedure pore 13. An osteotom with a diameter of 2.8 mm is insertedly fitted to the implant. The operator strikes the alveolar bone with a mallet to fracture the alveolar bone 12. After that, the alveolar bone is lifted as high as 1 mm, for instance.

Hence, the implant 20 has a damping effect. Even if the sinus membrane 12 is raptured, the alveolar bone or the implant is stopped from moving to the sinus 10. As mentioned in the prior art, damage on the sinus membrane 12 or rapture of the sinus membrane 12 could occur in the process of forming the procedure pore 13, when the operator is unaware. A numeral reference 14 is a penetrated portion of the sinus membrane 12.

Figure 3:
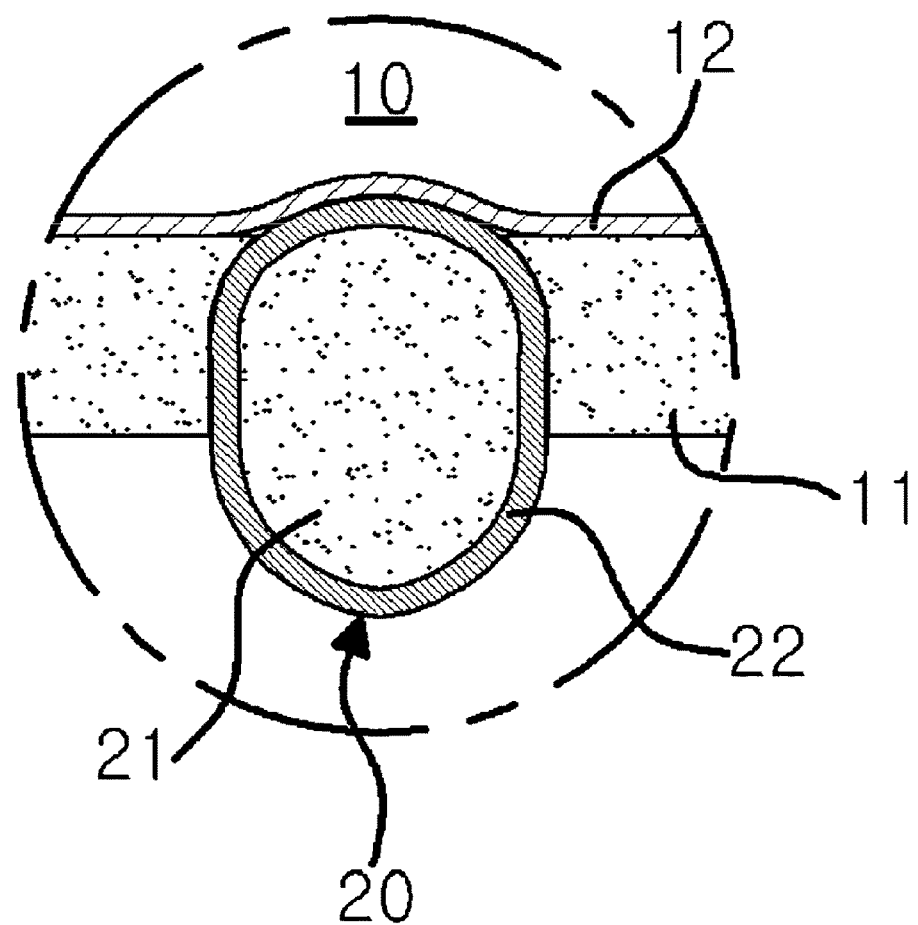

Following processes will be described, referring to FIGS. 3 through 5. FIG. 3 show a state where the implant 20 according to the embodiments of the present disclosure is inserted in the procedure pore 13. The protective film 22 covers the penetrated portion 14 of the sinus membrane 12 like a packing. Accordingly, the bone organism 21 is partially separated and blocked from moving to the sinus 10. When that state is kept for a preset time period, the sinus membrane 12 is restored as shown in FIG. 3. As more time passes, the protective film 22 is melted and dissolved as shown in FIG. 4. Then, the bone organism 21 is integrated with the alveolar bone 11 and a sufficient amount of the alveolar bone 11 to place the implant can be provided.

As shown in FIG. 5, the implant procedure is performed in earnest. An artificial dental root 30 is placed and an artificial tooth 31 is fixedly overlaid on the artificial dental root 30. At this time, a numeral reference 15 means a skin.

Figure 6:
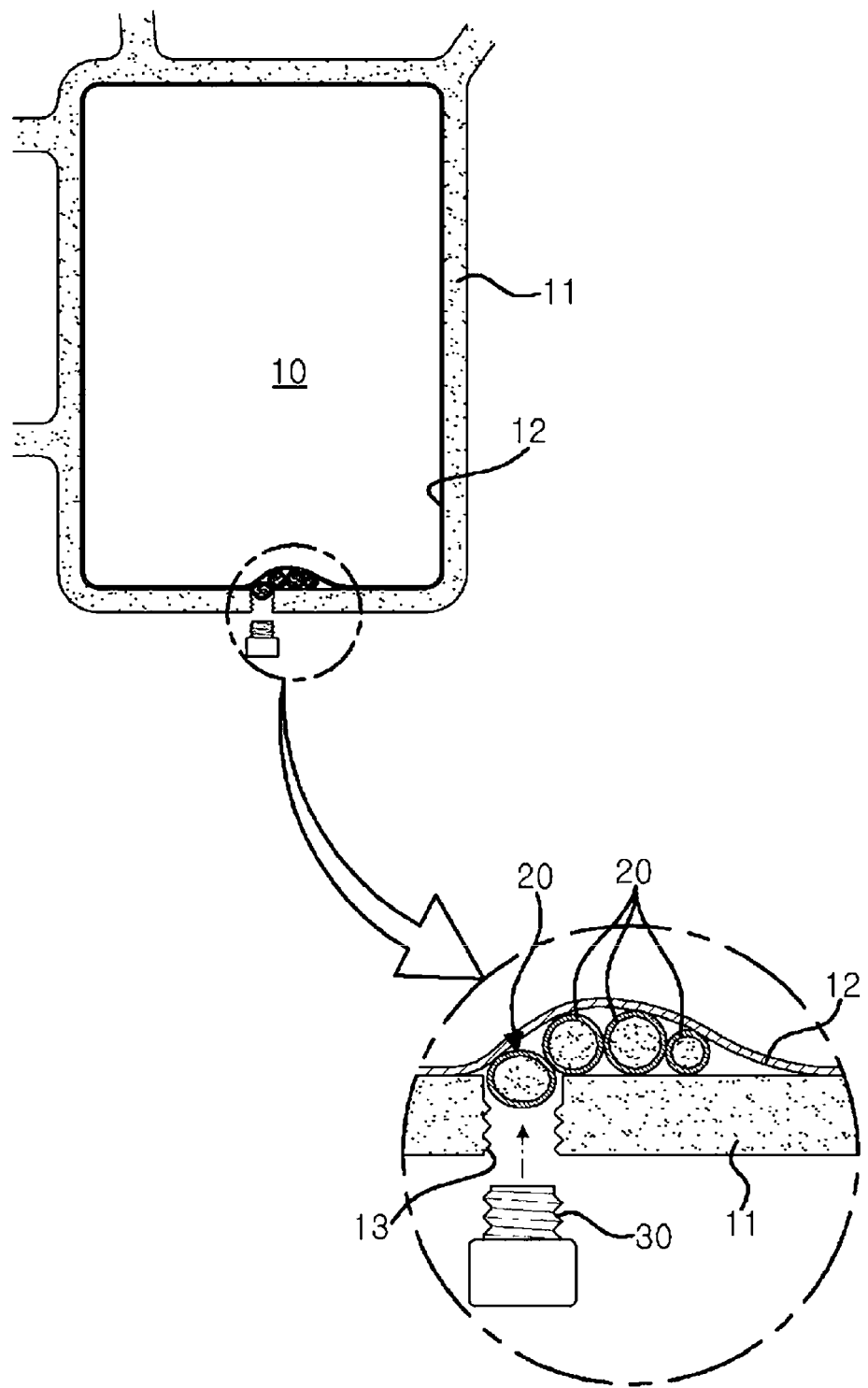
FIG. 6 is a diagram illustrating on example of a method for using the implant for the bone-graft according to exemplary embodiments of the present disclosure.
Figure 7:
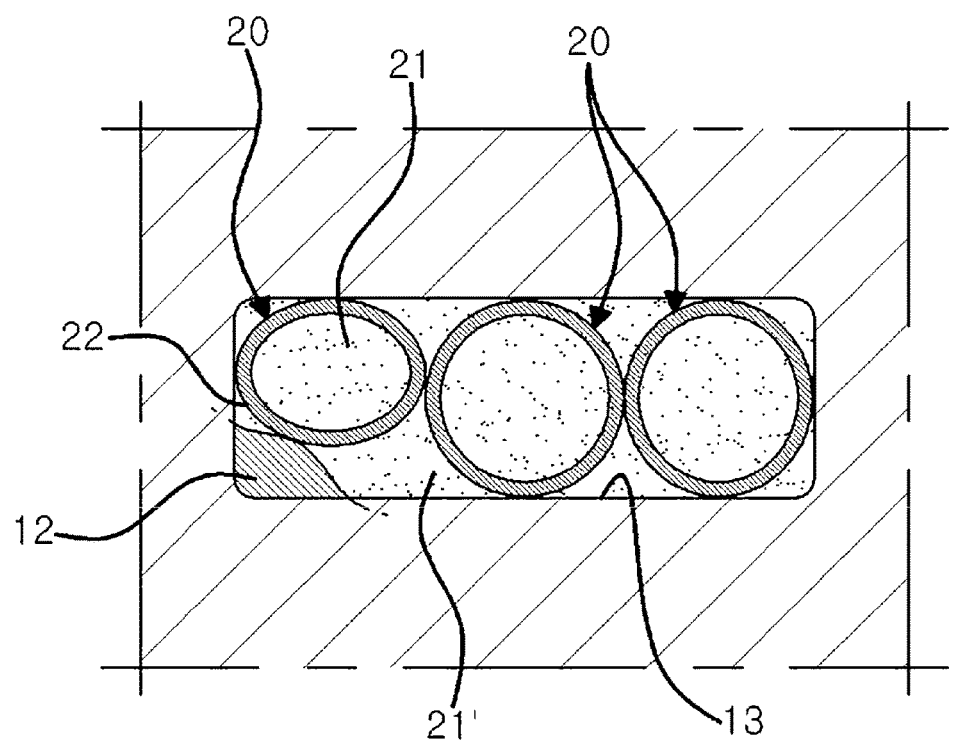
FIGS. 7 and 8 are diagrams illustrating a method for using the implant for bon-graft according to exemplary embodiments of the present disclosure.
Figure 8:
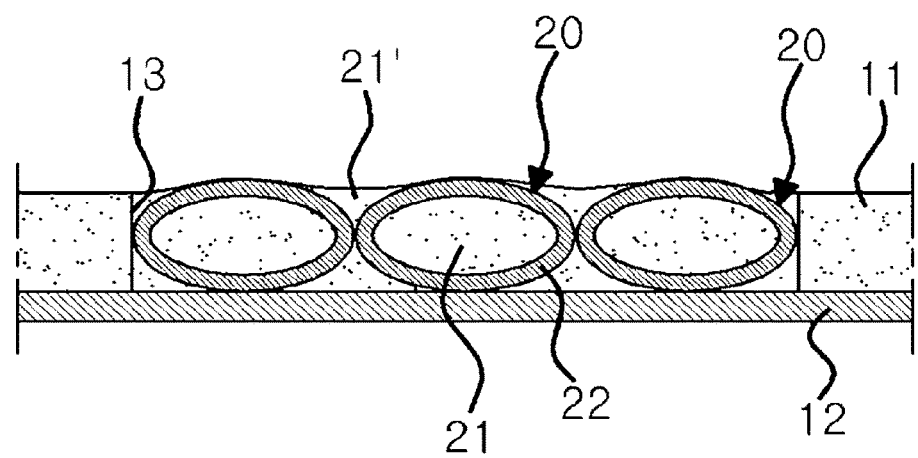

Referring to FIGS. 6 through 8, embodiments of the procedure method using the implant will be described. Referring to FIG. 6, a procedure method of the sinus lift will be described.

The procedure pore 13 is provided in the same method described above. The implant 20 for the bon-graft is equal to the one described above and repeated description thereof will be omitted accordingly. A plurality of implants 20 for bone-graft are used and the sizes of the implants may be variable. The implants 20 for the bone-graft are sequentially inserted in the procedure pore 13. Accordingly, the protective film 22 of the implant 20 for the bone-graft applies a pressure to the sinus membrane 12 to lift the sinus membrane 12 from a surface of the alveolar bone 11. The lift of the sinus membrane 12 and the bone-graft may be performed simultaneously, which is a core of the present disclosure. The artificial root 30 may be placed at the same time with the lift according to the patient's condition or it may be placed after a cut-away portion is healed.

Next, another embodiment of the procedure method will be described, referring to FIGS. 7 and 8. This embodiment provides a window surgery. The window surgery is a lateral approach method performed when the length of the alveolar bone 11 is 3 mm or less.

After anesthesia, a flap of an edentulous portion is cut away and the flap is open. After that, the flap is separated to a lower portion of a zygoma to secure a clear view. An oval window is formed in a bone located 3~4 mm down from a top of flap under main water of saline as round bur. A taken oval lid (not shown) is soaked in salt water and then a procedure pore 13 which is broad like a window is provided. Separation of the sinus membrane is performed from every direction of the procedure pore 13, using sinus curet. The implant for the bone-graft is inserted in the space generated after the separation. In this embodiment, the method of forming the procedure pore 13 is different from the method according to the former embodiment mentioned above.

The window-like procedure pore 13 is filled with the implant 20 for the bone-graft sequentially and a gap between them is then filled with a bone organism 21' for bone-graft, such that the procedure pore 13 can be filled with the bone organism 21' and the implant 20 together. In the method according to this embodiment, the artificial dental root (30, see FIG. 5 or 6) may be placed simultaneously with the bone-grafting or it may be placed after the healing of the affected area, according to the patient's condition.

Once the artificial dental root 30 is placed simultaneously together with the bone-graft, the oval-shaped lid is taken out of the saline to cover the procedure pore 13 and the flap is returned and sutured.

Various variations and modifications of the refrigerator described above are possible in the component parts and/or arrangements of the subject combination arrangement within the scope of the disclosure, the drawings and the appended claims. In addition to variations and modifications in the component parts and/or arrangements, alternative uses will also be apparent to those skilled in the art. For instance, the implant 20 for the bone-graft may be used in other diverse methods not described above and it may have diverse sizes and shapes.

What is claimed is:

1. A bone-grafting method using an implant for bone-graft insertedly placed in a procedure pore, the method includes:
   forming a procedure pore in an alveolar bone;
   lifting a sinus membrane by a pressure applied to the sinus membrane by sequentially filling a plurality of implants into the procedure pore; and
   filling a powder type bone organism for bone-graft in a gap between the implants,
   wherein the implants includes respectively a lump type bone organism, and a protective film, wherein an overall outer portion of the lump type bone organism is coated with the protective film,
   wherein the protective film is absorbed into a body and dissolved as time passes after the implants is insertedly placed in the procedure pore.

2. The method of claim 1, wherein the procedure pore is provided in an alveolar bone by drilling.

3. The method of claim 2, wherein the drilling is performed as deep as the alveolar bone remains.

4. The method of claim 1, wherein the lump type bone organism is an allograft bone, a heterograft bone, an autograft bone and a synthetic bone,
   wherein the allograft bone is cortical bone taken from a tissue donor, the cortical bone being frozen and dried without deliming.

5. The method of claim 1, wherein the protective film is a collagen extracted from a hetero-biological material.

* * * * *